US007795497B2

(12) United States Patent
Daniell

(10) Patent No.: US 7,795,497 B2
(45) Date of Patent: Sep. 14, 2010

(54) MARKER FREE TRANSGENIC PLANTS: ENGINEERING THE CHLOROPLAST GENOME WITHOUT THE USE OF ANTIBIOTIC SELECTION

(75) Inventor: Henry Daniell, Winter Park, FL (US)

(73) Assignees: University of Central Florida Research Foundation, Inc., Orlando, FL (US); Auburn University, Auburn, AL (US)

( * ) Notice: Subject to any disclaimer, the term of this patent is extended or adjusted under 35 U.S.C. 154(b) by 74 days.

(21) Appl. No.: 10/741,379

(22) Filed: Dec. 19, 2003

(65) Prior Publication Data

US 2004/0231015 A1 Nov. 18, 2004

Related U.S. Application Data

(63) Continuation of application No. 09/807,722, filed as application No. PCT/US01/06275 on Feb. 28, 2001, now abandoned.

(60) Provisional application No. 60/259,154, filed on Dec. 28, 2000, provisional application No. 60/257,406, filed on Dec. 22, 2000, provisional application No. 60/209,762, filed on Jun. 6, 2000, provisional application No. 60/186,308, filed on Mar. 2, 2000.

(51) Int. Cl.
*C12N 15/82* (2006.01)
(52) U.S. Cl. .................................. 800/278
(58) Field of Classification Search ................ None
See application file for complete search history.

(56) References Cited

U.S. PATENT DOCUMENTS 5,633,153 A * 5/1997 Ursin ..................... 800/293
5,693,507 A   12/1997 Daniell et al.
5,877,402 A * 3/1999 Maliga et al. ............ 800/298
5,932,479 A    8/1999 Daniell et al.
6,680,426 B2 * 1/2004 Daniell et al. ............ 800/293

FOREIGN PATENT DOCUMENTS

WO    WO 99/10513    3/1999
WO    WO 00/03022    1/2000

OTHER PUBLICATIONS

Daniell et al, 1994, NATO ASI Series vol. H 86:589-604.*
Rathinasabapathi et al, 1994, Planta 193:155-162.*
Holmstrom et al, 1994, Plant J. 6:749-758.*
Arntzen, C. J. et al. "Edible Vaccines", *Public Health Reports*, May/Jun. 1997, pp. 190-197, vol. 112.
Bock, R. et al. "Extracellular inheritance: Plastid Genomics: Manipulation of Plastid Genomes and Biotechnology Apparatus", *Progress in Botany*, 2000, pp. 76-90, vol. 6.
Bogorad, L. et al. "Engineering Chloroplasts: An Alternative Site for Foreign Genes, Proteins, Reactions and Products", *Trends in Biotechnology*, 2000, pp. 257-263, vol. 18.
Boynton, J. E. et al. "Chloroplast Transformation in Chlamydomonas with High Velocity Microprojectiles", 1998, pp. 1534-1538.
Brixey, P. J. et al. "The Chloroplast psbA Promoter is More Efficient in *Escherichia coli* than the T7 Promoter for Hyperexpression of a Foreign Protein" 1997, *Biotechnology Letters*, pp. 395-399.
Carlson, P. S. et al. "The Use of Protoplasts for Genetic Research", 1973, pp. 598-602, vol. 70, No. 2.
Chaleff, R.S. et al. "Herbicide-Resistant Mutants from Tobacco Cell Cultures", 1984, *Science*, vol. 223.
Comai, L. et al. "An Altered aroA Gene Product Confers Resistance to the Herbicide Glyphosate", 1983, *Science*, pp. 370-371, vol. 221.
Daniell, H. "Transformation and Foreign Gene Expression in Plants Mediated by Microprojectile Bombardment", *Meth. Mol. Biol.*, 1997, pp. 453-488, vol. 62.
Daniell, H. et al. "GM Crops: Public Perception and Scientific Solutions" *Trends in Plant Science*, Dec. 1999, pp. 467-469, vol. 4, No. 12.
Daniell, H. et al. "Foreign Gene Expression in Chloroplasts of Higher Plants Mediated by Tungsten Particle Bombardment" *Methods in Enzymology*, pp. 536-556, vol. 217, 1993.
Daniell, H. "New Tools for Chloroplast Genetic Engineering" *Nature Biotechnology*, 1999, pp. 855-856, vol. 17.
Daniell, H. et al. "Containment of Herbicide Resistance Through Genetic Engineering of the Chloroplast Genome", *Nature Biotechnology*, 1998, pp. 345-348, vol. 16.
Daniell, H. et al. "Hyperexpression of Synthetic Protein-Based Polymer Gene" *Method. Mol. Biol.*, 1997, pp. 359-371, vol. 63.
Daniell, H. et al. "Biopolymer Production in Microorganisms and Plants", *Chemistry and Industry*, 1997, pp. 555-558, vol. 4.
Daniell, H. et al. "Transient Expression of β-glucuronidase in Different Cellular Compartments Following Blolistic Delivery of Foreign DNA into Wheat Leaves and Calli", *Plant Cell Reports.*, 1991, pp. 615-619, vol. 9.
Daniell, H. "Uptake and Expression of Bacterial and Cyanobacterial Genes by Isolated Cucumber Etioplasts" *Proc. Natl. Acad. Sci. USA*, 1987, pp. 6349-6353, vol. 84.
Daniell, H. et al. "Transient Foreign Gene Expression in Chloroplasts of Cultured Tobacco Cells After Biolistic Delivery of Chloroplast Vectors", *Proc. Natl. Acad. Sci. USA*, 1990, pp. 88-92, vol. 87.
Daniell, H. et al. "Engineering Plants for Stress Tolerance Via Organelle Genomes", *NATO ASI Series*, 1994, pp. 589-604., vol. H86.
Daniell, H. et al. "In Vitro Synthesis of Photosynthetic Membranes: I. Development of Photosystem I Activity and Cyclic Photophosphorylation", *Biochemical and Biophysical Res. Comm.*, 1983, pp. 740-749, vol. 111, No. 2.
Daniell, H. et al. "Chloroplast Culture IX Chlorophyll (IDE) a Biosynthesis In Vitro at Rates Higher Than In Vivo", *Biochemical and Biophysical Res. Comm.*, 1982, pp. 740-749, vol. 106, No. 2.

(Continued)

*Primary Examiner*—Anne R Kubelik
(74) *Attorney, Agent, or Firm*—Timothy H. Van Dyke; Beusse Wolter Sanks Mora & Maire

(57) ABSTRACT

The present invention provides for a method to circumvent the problem of using antibiotic resistant selectable markers. In particular, target plants are transformed using a plastid vector which contains heterologous DNA sequences coding for a phytotoxin detoxifying enzyme or protein. The selection process involves converting a antibiotic-free phytotoxic agent by the expressed phytotoxin detoxifying enzyme or protein to yield a nontoxic compound. The invention provides for various methods to use antibiotic-free selection in chloroplast transformation.

10 Claims, 11 Drawing Sheets

OTHER PUBLICATIONS

Dankocsik, C. et al. "Activation of a Cryptic Crystal Protein Gene of *Bacillus thuringiensis* subspecies *kurstaki* by Gene Fusion and Determination of the Crystal Protein Insecticidal Specificity", *Mol. Microbiology*, 1990, pp. 2087-2094, vol. 4, No. 12.

De Block, M. et al. "Engineering Herbicide Resistance in Plants by Expression of a Detoxifying Enzyme", *The EMBO Journal*, 1987, pp. 5513-2518, vol. 6. No. 9.

De Cosa, B. et al. "Overexpression of the *Bt cry2*Aa2 Operon in Chloroplasts leads to formation of Insecticidal Crystals", *Nature Biotech.*, 2001, pp. 71-74, vol. 19.

Eibl, C. et al. "In Vivo Analysis of Plastid *psbA*, rbcL and pr/32 UTR Elements by Chloroplast Transformation: Tobacco Plastid Gene Expression is controlled by Modulation of Transcript Levels and Translation Efficiency", *The Plant Journal*, 1993, pp. 333-345, vol. 19, No. 3.

Erickson et al. "Herbicide Resistance in *Chlamydomonas Reinhardtii* Results from a Mutation in the Chloroplast Gene for the 32-Kilodalton Protein of Photosystem II" *Proc. Natl. Acad. Sci. USA*, 1984, pp. 3617-3621, vol. 81.

Falco, S. C. et al. "Genetic Analysis of Mutants of *Saccharomyces Cerevisiae* Resistant to the Herbicide Sulfometuron Methyl" *Genetics*, 1985, pp. 21-35, vol. 109.

Fischer, N. et al. "Selectable Marker Recycling in the Chloroplast" *Mol. Gen. Genet.*, 1996, pp. 373-380, vol. 251.

Fox, J. L. "GM Food Singled Out for Labeling in the US" *Nature Biotech.*, 2000, p. 375, vol. 18.

Gabard, J. M. et al. "Cross-Resistance to Short Residual Sulfonylurea Herbicides in Transgenic Tobacco Plants" *Plant Physiol.*, 1989, pp. 574-580, vol. 91.

Galloway, R. E. et al. "Atrazine, Bromacil, and Diuron Resistance in *Chlamydomonas*: A Single Non-Mendelain Genetic Locus Controls the Structure of the Thylakoid Binding Site" *Plant Physiol.*, 1984, pp. 469-474.

Golden, S. S. et al. "Mutation to Herbicide Resistance Maps Within the *psbA* Gene of *Anacystis nidulans* R2" *Science*, 1985, pp. 1104-1107, vol. 229.

Gonzalez, III, L. S. et al. "Aminoglycosides: A Practical Review", *Amer. Fam. Phys.*, 1998, pp. 1811-1818, vol. 58, No. 8.

Guda, C. et al. "Hyper Expression of an Environmentally Friendly Synthetic Polymer Gene" *Biotech. Letters*, 1995, pp. 745-750, vol. 17, No. 7.

Guda, C. et al. "Stable Expression of a Biodegradable Protein-Based Polymer in Tobacco Chloroplasts", *Plant Cell Rep.*, 2000, pp. 257-262, vol. 19.

Heifetz, P. B. "Genetic Engineering of the Chloroplast", *Blochimie*, 2000, pp. 655-666, vol. 82.

Hirschberg, J. et al. "Molecular Basis of Herbicide Resistance in *Amaranthus hybridus*" *Science*, pp. 1346-1349, vol. 222, 1983.

Hodgson, J. "Monarch *Bt*-corn Paper Questioned", *Nature Biotech.*, 1999, p. 627, vol. 17.

Hoyle, B. "Canadian Farmers Seek Compensation for 'Genetic Pollution'", *Nature Biotech.*, 1999, pp. 747-748, vol. 17.

Johanningmeier, U. et al. "A New Mutation in the Gene Coding for the Herbicide-Binding Protein in *Chlamydomonas*", *FEBS Letters*, 1987, pp. 221-224, vol. 211, No. 2.

Kanyand, M. et al. "Thidiazuron Promotes High Frequency Regeneration of Peanut (*Arachis hypogaea*) Plants In Vitro", *Plant Cell Rep.*, 1994, pp. 1-5, vol. 14.

Keeler, K. H. et al. "Movement of Crop Transgenes Into Wild Plants" *Herbicide Resistant Crops*, 1996, pp. 303-330, CRC Press Inc.

Keegstra, K. et al. "Protein Import and Routing Systems of Chloroplasts", *The Plant Cell*, 1999, pp. 557-570, vol. 11.

Kin-Ying et al. "Introduction and Expression of Foreign DNA in Isolated Spinach Chloroplasts by Electroporation", *The Plant Journal*, 1996, pp. 737-743, vol. 10, No. 4.

Kling, J. "Could Transgenic Supercrops One Day Breed Superweeds?", *Science*, 1996, pp. 180-181, vol. 274.

Kota, M. et al. "Overexpression of the *Bacillus thuringiensis* (Bt) Cry2Aa2 Protein in Chloroplasts Confers Resistance to Plants against Susceptible an dBt-resistant Insects", *Proc. Natl. Acad. Sci. USA*, 1999, pp. 1840-1845, vol. 96.

Laemmli, U. K. "Cleavage of Structural Proteins During the Assembly of the Head of Bacteriophage T4", *Nature*, 1970, pp. 680-685, vol. 227.

Langevin, S. A. et al. "The Incidence and Effects of Hybridization Between Cultivated Rice and Its Related Weed Red Rice", *Evolution*, 1990, pp. 1000-1008, vol. 44, No. 4.

Llewellyn, D. et al. "Pollen Dispersal from Two Field Trials of Transgenic Cotton in the Namoi Valley, Australia", *Mol. Breeding*, 1996, pp. 157-166, vol. 2.

Losey, J. E. et al. "Transgenic Pollen Harms Monarch Larvae" *Nature*, 1999, p. 214, vol. 399.

Lu, Z. et al. "Characterization of Republication Origins Flanking the 23S rRNA Gene in Tobacco Chloroplast DNA", *Plant Mol. Biol.*, 1996, pp. 693-706, vol. 32.

Maier, R. M. et al. "Complete Sequence of the Maize Chloroplast Genome: Gene Content, Hotspots of Divergence and Fine Tuning of Genetic Information by Transcript Editing", *J. Mol. Biol.*, 1995, pp. 614-628, vol. 251.

Miele, L. "Plants as Bioreactors for Biopharmaceuticals: Regulatory Consideration" *TIB Tech.*, 1997, pp. 45-49, vol. 15.

McBride, K. E. et al. "Amplification of a Chimeric *Bacillus* Gene in Chloroplasts Leads to an Extraordinary Level of an Insecticidal Protein in Tobacco" *Biotechnology*, 1995, pp. 362-365, vol. 13.

Nielson, B. L. et al. "Characterization of the Pea Chloroplast DNA *Ori*A Region", *Plasmid*, 1993, pp. 197-211, vol. 30.

Nuccio, M. L. et al. "Metabolic Engineering of Plants for Osmotic Stress Resistance", *Curr. Opinion Plant Biol.*, 1999, pp. 128-134, vol. 2.

Oard, J. H. et al. "Development, field evaluation, and agronomic Performance of Transgenic Herbicide Resistance Rice", *Mol. Breeding*, 1996, pp. 359-368, vol. 2.

Peerenboom, E. et al. "German Health Minister Calls Time Out for Bt Maize", *Nature Biotech.*, 2000, p. 374, vol. 18.

Penaloza-Vazquez, A. et al. "Expression of the Hygromycin B Phosphotransferase Gene Confers Tolerance to the Herbicide Glyphosate" *Plant Cell Rep.*, 1995, pp. 482-487, vol. 14.

Rathinasabapathi, K. F. et al. "Metabolic Engineering of Glycine Betaine Synthesis: Plant Betaine Aldehyde Dehydrogenases Lacking Typical Transit Peptides are Targeted to Tobacco Chloroplasts where they Confer Betaine Aldehyde Resistance", *Planta*, 1994, pp. 155-162, vol. 193.

Rudraswamy, V. et al. "Plastid-Transformed Rice" *In Vitro Cell. Dev. Biol.—Animal*, 1999, p. 1085, vol. 35, No. 3, (http://altweb.jhsph.edu/publications/journals/iva/iva35_3suppl/iva35_3supp110b.htm).

Sanford, J. C. "The Biolistic Process", *Trends In Biotech.*, 1988, pp. 299-302, vol. 6.

Sankula, S. et al. "Evaluation of Glufosinate on Rice (*Oryza sativa*) Transformed with the BAR Gene and Red Rice (*Oryza sativa*)", *Weed Tech.*, 1997, pp. 70-75, vol. 11.

Sidorov, V. A. et al. "Stable Chloroplast Transformation in Potato: Use of Green Fluorescent Protein as a Plastid Marker", *The Plant Journal*, 1999, pp. 209-216, vol. 19, No. 2.

Sijmons, P. C. et al. "production of Correctly Processed Human Serum Albumin in Transgenic Plants", *Bio/Tech.*, 1990, pp. 217-221.

Stalker, D. M. et al. "A Single Amino Acid Substitution in the Enzyme 5-Enolpyruvylshikimate-3-Phosphate Synthase Confers Resistance to the Herbicide Glyphosate", *J. Biol. Chem.*, 1985, pp. 4724-4728, vol. 260, No. 8.

Stummann, B. M. et al. "Nucleotide Sequence of the Single Ribosomal RNA Operon of Pea Chloroplast DNA", *Physiol. Plant.*, 1988, pp. 139-146, vol. 72.

Svab, Z. et al. "High-Frequency Plastid Transformation in Tobacco by Selection for a Chimeric *aadA* Gene" *Proc. Natl. Acad. Sci. USA*, 1993, pp. 913-917, vol. 90.

Svab, Z. et al. "Stable Transformation of Plastids in Higher Plants" *Proc. Natl. Acad. Sci. USA*, 1990, pp. 8526-8530, vol. 87.

Scott, S. E. et al. "Low Probability of Chloroplast Movement from Oilseed Rape (*Brassica napus*) into Wild *Brassica Rapa*", *Nature Biotech.*, 1999, pp. 390-392.

Umbeck, P. F. et al. "Degree of Pollen Dispersal by Insects form a Field Test of Genetically Engineered Cotton", *j. Econ. Entomol.*, 1991, pp. 1943-1950, vol. 84, No. 6.

Weretilnyk, E. A. et al. "Comparative Biochemical and Immunological Studies of the Glycine Betaine Synthesis Pathway in Diverse Families of Dicotyledons" *Planta*, 1989, pp. 342-352, vol. 178.

Widner, W. R. et al. "Two Highly Related Insecticidal Crystal Proteins of *Bacillus Thuringiensis* Subsp. *Kurstaki* Posses Different Host Specificities", *J. Bacter.*, 1989, pp. 965-974, vol. 171, No. 2.

Yavad et al. "Single Amino Acid Substitutions in the Enzyme Acetolacate Synthase Confer Resistance to the Herbicide Sulfometuron Methyl", *Proc. Natl. Acad Sci. USA*, 1986, pp. 4418-4422, vol. 83.

Ye, G. N. et al. "Optimization of Delivery of Foreign DNA into Higher-Plant Chloroplasts", *Plant Mol. Biol.*, 1990, pp. 809-819, vol. 15.

Yeh, H. et al. "Sequence Variation of Bovine Elastin mRNA Due to Alternative Splicing", *Coll. Relat. Res.*, 1987, pp. 235-247, vol. 7. No. 4. [abstract only].

Zheng, Q. et al. "Rapid and Repetitive Plant Regeneration in Sweet Potato via Somatic Embryogenesis", *Plant Cell Rep.*, 1996, pp. 381-385, vol. 15.

Zhang, X. et al. "Nuclear Expression of an Environmentally Friendly Synthetic Protein Based Polymer Gene in Tobacco Cells", *Biotech. Letters*, 1995, pp. 1279-1284, vol. 17, No. 12.

Zhang, X. et al. "Expression of an Environmentally Friendly Synthetic Protein-Based Polymer Gene in Transgenic Tobacco Plants", *Plant Cell Rep.*, 1996, pp. 174-179, vol. 16.

Powles, S. B. et al. *Herbicide Resistance in Plants, Biology and Biochemistry*, 1994, eds. CRC, Press, Inc.

Basava, C. *Peptides: Design, Synthesis, and Biological Activity*, 1994, eds. Birkhauser, Boston.

\* cited by examiner

RI:EcoRI, RV:EcoRV, Nt:NotI, Xb:XbaI,
Ct:Chloroplast

3M: CCGCGTTGTTTCATCAAGCCTTACG (SEQ ID NO:1)
3P: AAAACCCGTCCTCAGTTCGGATTGC (SEQ ID NO:2)

Table 1: Comparison of Spectinomycin and Betaine aldyhyde as the selectable marker for the first round of selection.

| Selectable marker | Plate No. | Total no. of leaf discs | No. of responding leaf discs | Total no. of shoots/ plate |
|---|---|---|---|---|
| BADH | 1 | 3 | 3 | 43 |
| BADH | 2 | 6 | 4 | 23 |
| BADH | 3 | 11 | 9 | 33 |
| BADH | 4 | 7 | 6 | 19 |
| BADH | 5 | 6 | 4 | 16 |
| BADH | 6 | 9 | 7 | 18 |
| Spectinomycin | 1 | 5 | 0 | 0 |
| Spectinomycin | 2 | 5 | 0 | 0 |
| Spectinomycin | 3 | 5 | 3 | 3 |
| Spectinomycin | 4 | 5 | 2 | 2 |
| Spectinomycin | 5 | 5 | 0 | 0 |
| Spectinomycin | 6 | 5 | 1 | 1 |
| Spectinomycin | 7 | 5 | 1 | 2 |
| Spectinomycin | 8 | 5 | 1 | 2 |
| Spectinomycin | 9 | 5 | 0 | 0 |
| Spectinomycin | 10 | 5 | 0 | 0 |
| Control | | 5 | 0 | 0 |

MARKER FREE TRANSGENIC PLANTS: ENGINEERING THE CHLOROPLAST GENOME WITHOUT THE USE OF ANTIBIOTIC SELECTION

CROSS-REFERENCE TO RELATED APPLICATIONS

This application is a continuation application of application Ser. No. 09/807,722; filed Apr. 18, 2001 (now abandoned); which application was a national stage application of international application PCT/US01/06275; filed Feb. 28, 2001; which claims the benefit of provisional patent applications Ser. No. 60/259,154; filed Dec. 28, 2000; Ser. No. 60/257,406; filed Dec. 22, 2000; Ser. No. 60/209,762; filed Jun. 6, 2000; and Ser. No. 60/186,308; filed Mar. 2, 2000.

STATEMENT REGARDING FEDERALLY SPONSORED RESEARCH

The work of this invention is supported in part by the USDA-NRICGP grants 95-82770, 97-35504 and 98-0185 to Henry Daniell.

FIELD OF THE INVENTION

This application pertains to the field of genetic engineering of plant plastid genomes, particularly chloroplasts, and to methods of and engineered plants without the use of antibiotics.

This application relates in particular to a method of selecting genetically engineered or transformed plants without the use of antibiotics as a selectable marker. The application also relates to a method of transforming plants to confer drought tolerance and to the transformed plants which are drought tolerant.

DESCRIPTION OF THE RELATED ART

Publications

Various methods of selection of plants that employ antibiotic-free selectable marker, or non-antibiotic selectable markers, have been described in the past.

Briggs, in U.S. Pat. No. 5,589,611 (Dec. 31, 1996) entitled "Disease resistance gene from maize and its use for disease resistance as a selectable marker and as a gene identification probe," proposed a method of identifying transformed plants which is disease resistant. A gene that controls resistance to both a fungus and a fungal disease toxin is proposed as a selectable marker to identify transformed plants, particularly in maize. An expression cassette containing the DNA sequence of a disease resistance gene, namely the Hm1 gene in maize, is inserted into the nucleic genome of the plant cells. The transformed plants will be capable of producing HC-toxin reductase. By culturing the cells in growth medium containing the corresponding toxin produced by the pathogen, namely *Cocholiobolus carbonum* Nelson race 1, the lethal selection of transformed plants will result.

Ursin, in U.S. Pat. No. 5,633,153 (May 27, 1997) entitled "Aldehyde dehydrogenase selectable markers for plant transformation," proposed a method of using an aldehyde dehydrogenase as a selectable marker for nuclear transgenic plant cells. A DNA construct coded for an aldehyde dehydrogenase through eukaryotic promoters used for nuclear transformation and culturing such transformed cells in growth media containing the corresponding phytotoxic aldehyde, the transformed plants demonstrate resistance to the phytotoxic aldehyde.

Song, in U.S. Pat. No. 5,965,727 (Oct. 12, 1999), entitled "For selectable markers and promoters for plant tissue culture transformation," proposed transforming nuclear genome of plant cells with an expression cassette which contains DNA sequences coded for both the ASA2 promoter sequence of *Nicotiana tabacum*, or fragments thereof, that are capable of directing tissue culture specific expression. The ASA2 gene which is substantially resistant to inhibition by free L-Trp or an amino acid analog of Trp. When such cells are cultured in a medium containing an amount of an amino acid analog of Trp, successfully transformed plant cells survive.

Several patents have also discussed the conferring of osmoprotection to plants through plant transformation. Adams, in U.S. Pat. No. 5,780,709 (Jul. 14, 1998) entitled "Transgenic maize with increased mannitol content", proposed a method of conferring resistance to water or salt stress or altering the osmoprotectant content of a monocot plant by nucleic transformation. Transformation is accomplished via a vector containing an expression cassette comprised of a preselected DNA segment combined with a eukaryotic promoter functional in plant nucleus. Thus, the preselected DNA segment that was used to transform the monocot plants was the mt1D gene which encodes for the enzyme that catalyzes the synthesis of mannitol. Adams focused on the osmoprotective properties of sugar alcohols, specifically mannitol.

Wu, in U.S. Pat. No. 5,981,842 (Nov. 9, 1999), proposed that osmoprotection can be conferred upon cereal plants by transforming cereal plant cells or protoplasts with a promoter and a nucleic acid encoding a group 3 late embryogenesis protein (LEA protein) such as the HVA1 gene from barley. The transformed cereal plant accumulates HVA1 protein in both leaves and roots. The transformed plants showed an increase tolerance to drought and salt stress which correlated with the level of the HVA1 protein accumulated in the transformed plants.

All publications and patent applications are herein incorporated by reference.

BACKGROUND OF THE INVENTION

Disadvantages of the antibiotic selectable marker system. Most transformation techniques co-introduce a gene that confers antibiotic resistance, along with the gene of interest to impart a desired trait. Regenerating transformed cells in antibiotic containing growth media permits selection of only those cells that have incorporated the foreign genes as the gene of interest. Once transgenic plants are regenerated, antibiotic resistance genes serve no useful purpose but they continue to produce their gene products. One of the primary concerns of genetically modified (GM) crops is the presence of clinically important antibiotic resistance gene products in transgenic plants that could inactivate oral doses of the antibiotic (reviewed by Puchta 2000; Daniell 1999A). Another concern is that the antibiotic resistant genes could be transferred to pathogenic microbes in the gastrointestinal tract or soil rendering them resistant to treatment with such antibiotics. Antibiotic resistant bacteria are one of the major challenges of modern medicine. In Germany, GM crops containing antibiotic resistant genes have been banned from release (Peerenboom 2000).

Plastid genetic engineering as an alternative to nuclear genetic engineering. Plastid genetic engineering, particularly chloroplast genetic engineering, is emerging as an alternative new technology to overcome some of the environmental concerns of nuclear genetic engineering (reviewed by Bogorad, 2000). One common environmental concern is the escape of foreign gene through pollen or seed dispersal from transgenic crop plants to their weedy relatives creating super weeds or causing genetic pollution among other crops (Daniell 1999B). Keeler et al. (1996) have summarized valuable data on the weedy wild relatives of sixty important crop plants and potential hybridization between crops and wild relatives. Among sixty crops, only eleven do not have congeners and the rest of the crops have wild relatives somewhere in the world. In addition, genetic pollution among crops has resulted in several lawsuits and shrunk the European market of Canadian organic farmers (Hoyle 1999). Several major food corporations have required segregation of native crops from those "polluted" with transgenes. Two legislations have been submitted in the U.S. to protect organic farmers whose crops inadvertently contain transgenes via pollen drift (Fox 2000). Maternal inheritance of foreign genes through chloroplast genetic engineering is highly desirable in such instances where there is potential for out-cross among crops or between crops and weeds (Daniell et al. 1998; Scott and Wilkinson 1999; Daniell 1999C).

Yet another concern in the use of nuclear transgenic crops expressing the *Bacillus thuringiensis* (Bt) toxins is the suboptimal production of toxins resulting in increased risk of pests developing Bt resistance. Plant-specific recommendations to reduce Bt resistance development include increasing Bt expression levels (high dose strategy), expressing multiple toxins (gene pyramiding), or expressing the protein only in tissues highly sensitive to damage (tissue specific expression). All three approaches are attainable through chloroplast transformation (Daniell 1999C). For example, hyperexpression of several thousand copies of a novel B.t. gene via chloroplast genetic engineering, resulted in 100% mortality of insects that are up to 40.000-fold resistant to other B.t. proteins (Kota et al. 1999). Another hotly debated environmental concern expressed recently is the toxicity of transgenic pollen to non-target insects, such as the Monarch butterflies (Losey et al. 1999; Hodgson 1999). Although pollen from a few plants shown to exhibit maternal plastid inheritance contains metabolically active plastids, the plastid DNA itself is lost during the process of pollen maturation and hence is not transmitted to the next generation (reviewed in Heifetz, 2000, Bock and Hagmann, 2000). Lack of insecticidal protein in transgenic pollen engineered via the chloroplast genome with the cry2A gene has been demonstrated recently, even though chloroplast in leaves contained as much as 47% CRY protein of the total soluble protein (De Cosa et al. 2000).

The need for alternatives to the antibiotic selectable marker system. Despite these advantages, one major disadvantage with chloroplast genetic engineering in higher plants may be the utilization of the antibiotic resistance genes as the selectable marker to confer streptomycin/spectinomycin resistance. Initially, selection for chloroplast transformation utilized a cloned mutant 16S rRNA gene that does not bind the antibiotic and this conferred spectinomycin resistance (Svab et al. 1990). Subsequently, the aadA gene product that inactivates the antibiotic by transferring the adenyl moiety of ATP to spectinomycin/streptomycin was used (Svab and Maliga 1993). These antibiotics are commonly used to control bacterial infection in humans and animals. The probability of gene transfer from plants to bacteria living in the gastrointestinal tract or soil may be enhanced by the compatible protein synthetic machinery between chloroplasts and bacteria, in addition to presence of thousands of copies of the antibiotic resistance genes per cell. Also, most antibiotic resistance genes used in genetic engineering originate from bacteria.

Because of the presence of thousands of antibiotic resistant genes in each cell of chloroplast transgenic plants and the use of the most commonly used antibiotics in the selection process, it is important to develop a chloroplast genetic engineering approach without the use of antibiotics.

Non-obviousness of antibiotic free selection. Despite several advantages of plastid transformation, one major disadvantage with chloroplast genetic engineering in higher plants is the utilization of the antibiotic resistance genes as the selectable marker. Initially, selection for chloroplast transformation utilized a cloned mutant 16S rRNA gene that did not bind the antibiotic and this conferred spectinomycin resistance. Subsequently, the aadA gene was used as a selectable marker. Aminoglycoside 3'-adenylyltransferase inactivates the antibiotic by transferring the adenyl moiety of ATP to spectinomycin/streptomycin. Unfortunately, bacterial infections in humans and animals are also controlled by using these antibiotics. The probability of gene transfer from plants to bacteria living in the soil or gastrointestinal tract may be enhanced by the compatible protein synthetic machinery between chloroplasts and bacteria, in addition to presence of thousands of copies of the antibiotic resistance genes per cell. Also, most antibiotic resistance genes used in genetic engineering originate from bacteria.

Prior to this invention, there was no report of modifying the plastid genome without the use of antibiotic selection. Daniell et al. (2001) reported the first genetic engineering of the higher plant chloroplast genome without the use of antibiotic selection. The betaine aldehyde dehydrogenase (BADH) gene from spinach was used as a selectable marker. The selection process involves conversion of toxic betaine aldehyde (BA) by the BADH enzyme to nontoxic glycine betaine, which also serves as an osmoprotectant. While it was known earlier that BADH was a plant enzyme, it could not be conclusively demonstrated that this was a chloroplast enzyme because it lacked the typical transit peptide found in all chloroplast proteins imported from the cytosol.

The absence of a typical transit peptide raised several questions about proper cleavage of BADH enzyme in the stroma within plastids to be fully functional. It was not known whether the BADH enzyme would be catalytically active without proper cleavage within plastids.

The nuclear BADH cDNA with high GC content was never anticipated to express well in the AT rich prokaryotic plastid compartment because the codon usage is very different between the prokaryotic chloroplast compartment and the eukaryotic nuclear compartment. Therefore, it was not obvious to express a nuclear gene in the plastid compartment.

When the chloroplast transformation system was developed, it was hypothesized that the transformation process is possible only under non-lethal selection. Accumulation of betaine aldehyde is toxic and lethal to plant cells. Therefore, it was not clear whether non-lethal selection was required for chloroplast transformation. This invention has confirmed that the only requirement was that the selection process should be specific to plastids, particularly chloroplasts.

Rapid regeneration of chloroplast transgenic plants obtained under BA selection was never anticipated or suggested in any prior art. Chloroplast transformation efficiency was 25 fold higher in BA selection than spectinomycin and this was never anticipated in any previous investigations. Higher efficiency of betaine aldehyde selection compared to spectinomycin should facilitate chloroplast transformation of many economically important crops, including cereals that are naturally resistant to spectinomycin, in addition to conferring salt/drought tolerance.

Use of genes that are naturally present in spinach for selection, in addition to gene containment, should ease public concerns regarding GM crops.

SUMMARY OF THE INVENTION

The invention provides for a method to circumvent the problem of genetic pollution through plastid transformation and the use antibiotic-free selectable markers. Antibiotic-free phytotoxic agents and their corresponding detoxifying enzymes or proteins are used as a system of selection. In particular, the betaine aldehyde dehydrogenase (BADH) gene from spinach has been used as a selectable marker. This enzyme is present only in chloroplasts of a few plant species adapted to dry and saline environments. The selection process involves conversion of toxic betaine aldehyde (BA) by the chloroplast BADH enzyme to nontoxic glycine betaine (GB), which also serves as an osmoprotectant.

The preferred embodiment of this invention provides a method of selecting plant transformants using a plastid vector that includes a promoter targeted to the plastid, a DNA sequence encoding a gene of interest, another DNA sequence encoding a selectable marker such as an aldehyde dehydrogenase, and a terminator sequence. The transformed plants are selected by allowing transformed plants to grow in medium with the effective amount of a phytotoxin which is detoxified by the encoded aldehyde dehydrogenase. Lethal selection of the plants transformants will result.

It is another embodiment of this invention, the vector is targeted to plant chloroplasts. This embodiment can be carried out using both the universal chloroplast vector and a vector which is universal. Preferably, the vector includes a ribosome binding site and a 5' untranslated region (5' UTR. A promoter functional in green or non-green plastids is to be used in conjunction with the 5'UTR The invention provides the application of a wide variety of plants species and plant parts, including flowers, fruits, cereals, and all major crop plants.

The invention also provides for the plants transformants engineered and selected a antibiotic-free selectable marker with preferably a target heterologous DNA sequence.

The invention also provides for a method of conferring drought tolerance to plants with a antibiotic-free selectable marker. The plants or plant cells are transformed through the chloroplast by a vector containing a promoter targeted to the chloroplast, a DNA sequence encoding betaine aldehyde dehydrogenase, DNA sequences encoding at least one gene of interest, and a terminator sequence. The transformed plants are selected by allowing transformed plants to grow in medium with the effective amount of a phytotoxin which is detoxified by the encoded aldehyde dehydrogenase. Lethal selection of the plants transformants will result. The plants so transformed will be capable of glycine betaine production that leads to enhanced drought tolerance.

Table 1 shows the comparison of spectinomycin and betaine aldehyde as the selectable marker for the first round of selection.

DESCRIPTION OF THE SEQUENCES

SEQ ID NO: 1 is a nucleotide sequence of primer 3M.
SEQ ID NO: 2: is a nucleotide sequence of primer 3P.

DETAILED DESCRIPTION OF THE INVENTION

The invention discloses a novel way of selecting transformed plants, wherein the plant's plastid genome is transformed via a vector targeted to the plastid, and the selectable markers used for such transformation is a antibiotic-free marker. The invention further consists of the plants transformed and selected using the present method. The invention also discloses a method to confer osmoprotection to plants through chloroplast transformation.

The present invention is applicable to all plastids of plants. These include chromoplasts which are present in the fruits, vegetables and flowers; amyloplasts which are present in tubers like the potato; proplastids in roots; leucoplasts and etioplasts, both of which are present in non-green parts of plants.

The Vectors. This invention contemplates the use of vectors capable of plastid transformation, particularly of chloroplast transformation. Such vectors would include chloroplast expression vectors such as pUC, pBR322, pBlueScript, pGEM, and all others identified by Daniell in U.S. Pat. No. 5,693,507 and U.S. Pat. No. 5,932,479. Included are also vectors whose flanking sequence is located outside the inverted repeat of the chloroplast genome. These publications and patents are herein incorporated by reference to the same extent as if each individual publication or patent was specifically and individually indicated to be incorporated by reference.

A preferred embodiment of this invention utilizes a universal integration and expression vector competent for stably transforming the chloroplast genome of different plant species (Universal Vector). A universal vector is described in WO 99/10513 which was published on Mar. 4, 1999, which is herein incorporated in its entity.

The vector pLD-BADH was constructed by generating a PCR product using spinach cDNA clone as the template. The 5' primer also included the chloroplast optimal ribosome binding site (GGAGG). PCR product was subcloned into the EcoR1 site of pLD-CtV, resulting in pLD-BADH. BADH is one of the few proteins targeted to the chloroplast that lacks a definite transit peptide (Rathinasabapathi et al 1994). Authors suggest that information for transport may be contained within the mature protein. Even if a transit peptide was present, it should be cleaved in the stroma by the stromal processing peptidase (Keegstra and Cline, 1999). Furthermore, nuclear encoded cytosolic proteins with transit peptides have been successfully expressed within chloroplasts and found to be fully functional (Daniell et al. 1998). Therefore there was no need to delete any transit peptide.

Figure 1:
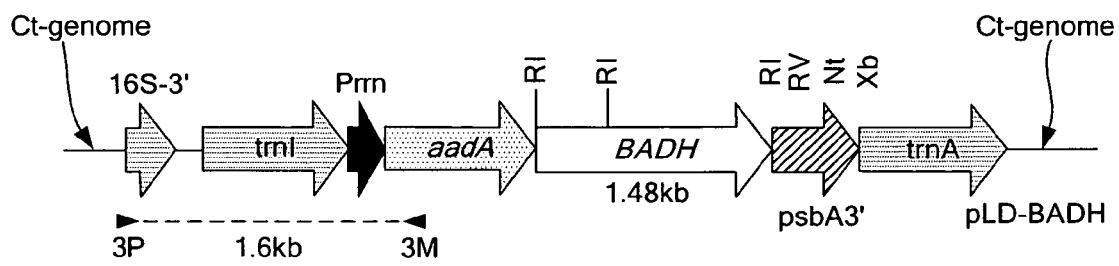
FIG. 1 shows the chloroplast universal vector pLD BADH. Primer 3P lands on the native chloroplast genome (in the 5' end region of 16-S r DNA gene). 3M lands on the aadA gene generating a 1.6 kb fragment. Restriction enzyme cut site are located on the map.

The universal vector, pLD-BADH, as shown in FIG. 1, integrates the aadA and BADH genes into the 16S-23S-spacer region of the chloroplast genome. Expression cassettes of the chloroplast integration vector contain the chimeric aadA gene and the BADH gene driven by the constitutive 16S rRNA promoter and regulated by the 3' untranslated region of the plastid psbA gene. The chimeric aadA gene encoding aminoglycoside 3'adenyltransferase confers spectinomycin resistance in chloroplasts enabling selection of the transformants on spectinomycin dihydrochloride. On the other hand, BADH converts the toxic betaine aldehyde in cells to glycine betaine. When present, this pathway is compartmentalized within chloroplasts (Nuccio, et al. 1999). To facilitate translation of the dicistronic mRNA, independent Shine-Dalgarno (SD) sequences were provided to the aadA and BADH genes upstream of the initiation codons. In order to accurately compare transformation efficiency of both selectable markers under identical bombardment and transformation conditions, aadA and BADH genes were inserted into the same vector, at the same site. Bombarded leaves were treated in identical manner except the addition of selection reagent.

Other plant specific vectors can be used to transform the plastids, particularly chloroplast, of various crops for betaine aldehyde selection. Some examples of these include the pLD-Alfa-BADH is for transforming the chloroplast genome of Alfalfa using betaine aldehyde selection; the pLD-Gm-utr-BADH is for transforming the chloroplast genome of Soybean (*Glycine max*) with betaine aldehyde; this contains the psbA promoter and untranslated region (UTR) for enhanced expression; the pLD-St-BADH is for transforming the chloroplast genome of potato (*Solanum tuberosum*) using betaine aldehyde selection; pLD-St-utr-BADH is for transforming the chloroplast genome of potato (*Solanum tuberosum*) with betaine aldehyde; this contains the psbA promoter and untranslated region (UTR) for enhanced expression; and the pLD-Tom-BADH is for transforming the chloroplast genome of tomato using betaine aldehyde selection.

Promoters. For transcription and translation of the DNA sequence encoding the gene of interest, the entire promoter region from a gene capable of expression in the plastid generally is used. The promoter region may include promoters obtained from green and non-green chloroplast genes that are operative upon the chloroplast, such as the psbA gene from spinach or pea, the rbcL, atpB promoter region from maize, the accD promoter and 16S rRNA promoter. Competent promoters are also described in U.S. Pat. No. 5,693,507, and the other literature sources contained therein. These publications and patents are herein incorporated by reference to the same extent as if each individual publication or patent was specifically and individually indicated to be incorporated by reference. Selectable markers. The preferred embodiment of this invention teaches the use of the spinach BADH gene as a selectable marker; wherein a plant is transformed via the chloroplast with the spinach BADH gene along with another nucleotide sequence encoding a desirable trait. The BADH gene product—betaine aldehyde dehydrogenase—will oxidize the betaine aldehyde in the growth medium allowing for the lethal selection of transformed plants.

Other forms of Antibiotic-Free Selection. Enzymes and proteins that function in plastids can be used as antibiotic-free phytotoxic agents. In case of amino acid biosynthesis, the synthesis is regulated by the substrate. When adequate amino acid is made, it binds to one of the enzymes in the pathway to block further synthesis (feed back inhibition). Mutant genes are available for many enzymes that are insensitive to such feed back inhibition. Such enzymes are expressed in the chloroplast by engineering feed back insensitive mutant genes via the chloroplast genome. Putative transgenic shoots are regenerated in a growth medium lacking specific amino acids. True transgenic plants will be regenerated in the growth medium. Thus, antibiotic free selection is accomplished.

Pigment biosynthesis can also be used in antibiotic free selection in plastids. While ancient plants (including pines) have the ability to synthesize chloroplhyll in the dark, flowering plants lost this capacity. This is because of the last step in chlorophyll biosynthesis is controlled by the enzyme protochlorophyllide reductase. This enzyme can function in the dark in primitive land plants and certain algae but is light dependent in higher plants. That is why ornamental plants kept inside the house requires light to synthesize chlorophyll. It is known that the chloroplast gene (chlB) for protochlorophyllide reductase in the green alga *Chlamydomonas* is required for light independent protochlorophyllide reductase activity (Plant Cell 5: 1817-1829). Therefore, chlB gene from the *Chlamydomonas* chloroplast is introduced into the chloroplast genome of higher plants and transgenic green shoots appearing in the dark is selected. Thus, pigment biosynthesis genes are used as antibiotic free selectable markers.

Another possibility is herbicide selection. Several methods can be used to genetically engineer herbicide resistance via the chloroplast genome. The target enzyme or protein is over-produced with 10,000 copies of foreign genes per transformed cell. This results in binding of all herbicide molecules thereby facilitating regeneration of transgenic shoots. Another approach is the use of modified enzyme or proteins (mutant) that does not bind the herbicide. The third approach is to use enzymes or proteins to breakdown the herbicide.

Drought tolerance likewise can be used as a selectable marker. Expression of the BADH enzyme or trehalose phosphate synthase via the chloroplast genome enables cells to tolerate drought. Drought conditions are created in culture plates by the addition of polyethylene glycol to the growth medium (3-6%). Only cells that express BADH or TPS are capable of drought tolerance and grows in the presence of polyethylene glycol. Thus, antibiotic free chloroplast transgenic plants are obtained.

Other Aldehyde Dehydrogenases. Other genes that code for an aldehyde dehydrogenase capable of detoxifying other phytotoxic aldehydes can be used in this novel selection system. These include, and are not limited to, genes that encode acetaldehyde dehydrogenase, formaldehyde dehydrogenase, proprionaldehyde dehydrogenase, and butyraldehyde dehydrogenase.

Plastid Transformation

The transformation of this invention maybe accomplished by any methods of transformation known in the art. Such methods include, but are not limited to PEG treatment, *Agrobacterium* treatment, and microinjection. Methods of transformation are described by Daniell et. al., "New Tools for Chloroplast Genetic Engineering," Nat. Biotechnology, 17:855-857 (1999). This publication is hereby incorporated by reference in its entirety. In the preferred embodiment, the method for transformation is by bombardment.

Figure 2:
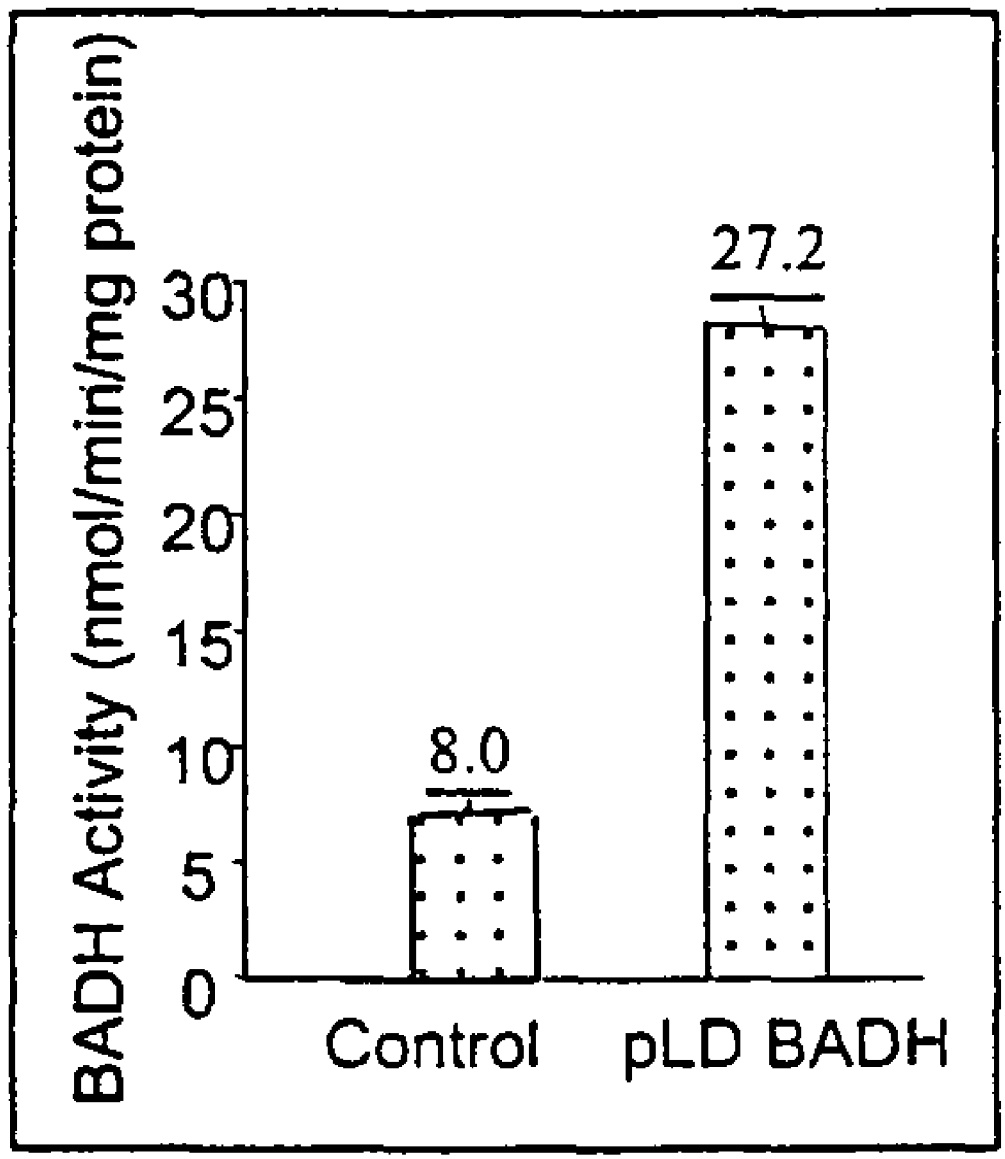
FIG. 2 shows BADH enzyme activity in *E. coli*. Cells harvested from overnight grown cultures were resuspended in a minimal volume of the assay buffer. Sonicated cell homogenate was desalted in G-25 columns and 50 µg total protein was used fr each assay. NAD+ dependent BADH enzyme was analyzed for the formation of NADH by increase in the absorbency at 340 nm.

The BADH gene expression was tested in *E. coli* cell extracts by enzyme assays before proceeding with bombardment. The universal vector pLD-BADH was transformed into the *E. coli* strain XL-1 Blue and grown in Terrific Broth (Guda et al. 2000) in the presence of ampicillin (100 μg/ml) at 37° C. for 24 hours. In *E. coli*, the level of expression by the chloroplast Prrn promoter is equivalent to that of the highly efficient T7 promoter and both systems have highly compatible protein synthetic machinery (Brixey et al. 1997). Therefore, BADH enzyme activity was tested in untransformed cells and cells transformed with pLD-BADH, a high copy number plasmid (FIG. 2). Crude sonic extracts isolated from transformed cells showed 3-5 fold more BADH activity than the untransformed control, confirming that the expression cassette is fully functional. This result also suggests that codon preference of the nuclear BADH gene is compatible with expression in the prokaryotic chloroplast compartment.

Tobacco (*Nicotiana tabacum* var. *Petit Havana*) was grown aseptically by germination of seeds in MSO medium. This medium contains MS salts (4.3 g/liter), B5 vitamin mixture (myoinositol, 100 mg/liter; thiamine-HCl, 10 mg/liter; nicotinic acid, 1 mg/liter; pyridoxine-HCI, 1 mg/liter), sucrose (30 g/liter) and phytagar (6 g/liter) at pH 5.8. Fully expanded, dark green leaves of about two month old plants were used for bombardment.

Leaves were placed abaxial side up on Whatman No. 1 filter papers laying on the RMOP medium (Daniell 1993) in standard petri plates (100×15 mm) for bombardment. Microprojectiles were coated with plasmid DNA (pLD-BADH) and bombardments were carried out with the biolistic device PDS 1000/He (Bio-Rad) as described by Daniell (1997). Following bombardment, petri plates were sealed with parafilm and incubated at 24° C. under 16 hour photoperiod. Two days after bombardment, leaves were chopped into small pieces of ~5 mm$^2$ in size and placed on the selection medium (RMOP containing 500 μg/ml of spectinomycin dihydrochloride or 5-10 mM betaine aldehyde) with abaxial side touching the medium in deep (100×25 mm) petri plates. The regenerated resistant shoots were chopped into small pieces (~2 mm$^2$) and subcloned into fresh deep petri plates containing the same selection medium. Resistant shoots from the second culture cycle were transferred to the rooting medium (MSO medium supplemented with IBA, 1 mg/liter containing appropriate selectable marker). Rooted plants were transferred to soil and grown at 26° C. under 16 hour photoperiod.

Selection and Heightened, Rapid Regeneration of Homoplasmic Transgenic Plants.

Figure 3:
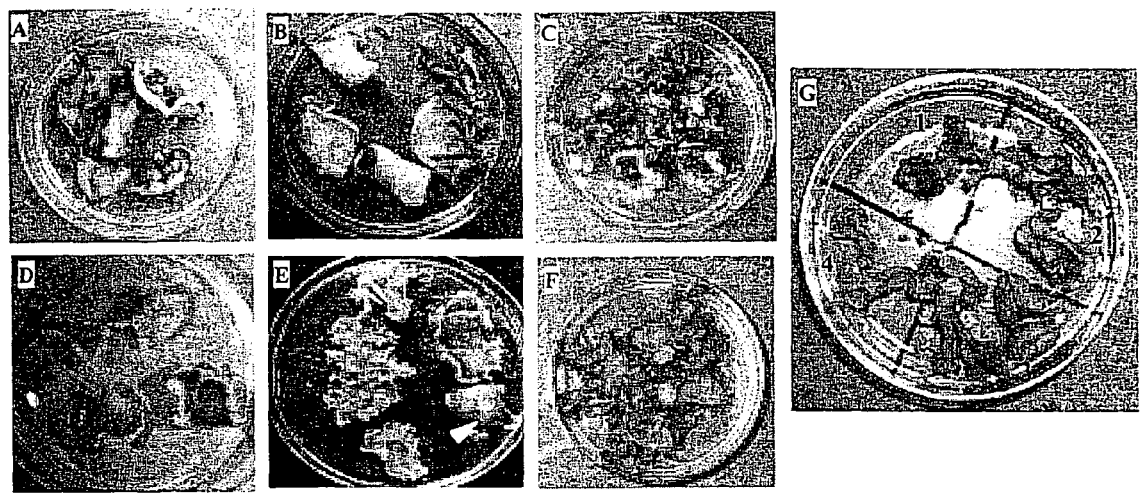
FIG. 3 shows a comparison of betaine aldehyde and spectinomycin selection. A. *N. tabacum* Petit Havana control in RMOP medium containing spectinomycin after 45 days. B. Bombarded leaf discs selected on spectinomycin in RMOP medium after 45 days. C. Spectinomycin resistant clones cultured again (sound round) to obtain homoplasmy. D. Petit Havana control in RMOP medium containing betaine aldehyde after 12 days of culture. E. Bombarded leaf discs selected on betaine aldehyde in RMOP medium after 12 days of culture; arrow indicates unbombarded leaf disc as control. Note that 23 shoots are formed on a disc selected on betain aldehyde against 1-2 shoots per disc on spectinomycin. F. Betaine aldehyde resistant clones cultureed again (second round) to obtain homoplasmy. G. Selection on 10 mM betaine aldehyde of untransformed (1) and transgenic (2-4) leaf discs. Note shoots from transgenic leaf discs and death of untransformed leaf disc.

The entire process of regeneration, starting from bombardment until transfer to soil, takes about 3-6 months for spectinomycin selection and 2-3 months for betaine aldehyde selection. FIG. 3 and Table 1 show differences between the two selection processes. Under spectinomycin selection, leaf discs continued to grow but pigments were bleached; resistant clones formed green shoots in about 45 days (FIG. 3B). On the other hand, under betaine aldehyde selection, growth of the leaf discs was completely inhibited and photosynthetic pigments were degraded (FIG. 3G-1), resistant clones formed green shoots within 12 days (FIG. 3E). Leaf disks in FIG. 3 under betaine aldehyde selection appear partially green because they were photographed 12 days after the initiation of the selection process whereas the disc photographed on spectinomycin were 45 days after initiation of the selection process. In spite of the short period of selection one leaf disk was almost bleached (FIG. 3D) and all of them were killed after 30 days. Under 10 mM betaine aldehyde selection, control untransformed samples were killed (turned black, 3G-1) whereas transgenic leaves produced new shoots (FIG. 3G, 2-4).

When the leaf discs were selected for spectinomycin resistance, only 15% of the discs responded and an average of one resistant shoot per plate was observed after 45 days. From each callus, all resistant shoots are considered to represent an individual clone. Under betaine aldehyde selection 80% of the discs responded and an average of 25 resistant shoots per plate was observed. Responding leaf disks formed one or two resistant shoots under spectinomycin selection whereas under betaine aldehyde selection, as many as 23 shoots were observed from a single leaf disk. Overall, 10 resistant shoots were regenerated from ten bombardments under spectinomycin selection while more than 150 shoots were recovered from six bombardments under betaine aldehyde selection. Therefore, the efficiency of transformation is 25 fold higher in betaine aldehyde selection than spectinomycin selection. Additionally, the latter procedure results in rapid regeneration.

Lethal Selection. The prior art suggests that chloroplast transformation system is possible only under non-lethal selection (Svab and Maliga 1993). This invention distinctly shows that this is not the case. Non-lethal selection was defined in the chloroplast transformation literature as lack of suppression of growth on the selection medium and that this was an absolute requirement for plastid transformation (Staub and Maliga 1993). It is known that accumulation of betaine aldehyde is toxic and lethal to plant cells (Rathinasabapathi et. al. 1994). This invention confirm earlier observations that betaine aldehyde is toxic to plant cells and inhibits growth. Therefore, this invention teaches that non-lethal selection is not a requirement for plastid transformation. The only requirement is that the selection process should be specific to plastids.

Confirmation of Chloroplast Integration, Homoplasmy and Copy Number.

Figure 4:
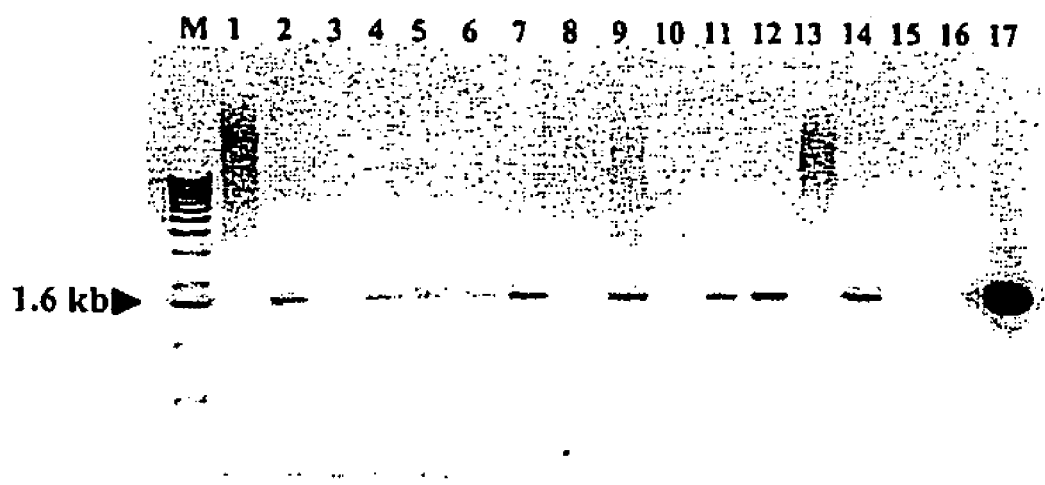
FIG. 4 shows the PCR analysis of DNA extracted from transformed plants run on a 0.8% agarose gel. Lane M 1 kb ladder, lane 1, untransformed Petit Havana control, lane 17 is positive control and lanes 2 through 16 are transgenic clones. Except lanes 10, 13, 15 and 16 all other lanes show the integration of aadA gene into the chloroplast genome.

Integration of a foreign gene into the chloroplast genome was confirmed by PCR screening of chloroplast transformants (FIG. 4). Primers were designed to eliminate mutants, nuclear integration and to determine whether the integration of foreign genes had occurred in the chloroplast genome at the directed site by homologous recombination. The strategy to distinguish between nuclear and chloroplast transgenic plants was to land one primer (3P) on the native chloroplast genome adjacent to the point of integration and the second primer (3M) on the aadA gene (FIG. 1). This primer set generated 1.6 kb PCR product in chloroplast transformants (FIG. 4). Because this product cannot be obtained in nuclear transgenic plants, the possibility of nuclear integration can be eliminated. PCR screening for chloroplast transformants after the first culture cycle showed that 11 out of 15 betaine aldehyde resistant clones integrated foreign genes into the chloroplast genome. The rest of the resistant shoots may be either escapes or nuclear transformants. Hence, only PCR positive clones were advanced to further steps of regeneration. In contrast, nearly 60% of the spectinomycin resistant clones were mutants. Other labs have recently reported as high as 90% mutants among spectinomycin resistant clones (Eibl et al. 1999; Sidorov et al. 1999).

Figure 5:
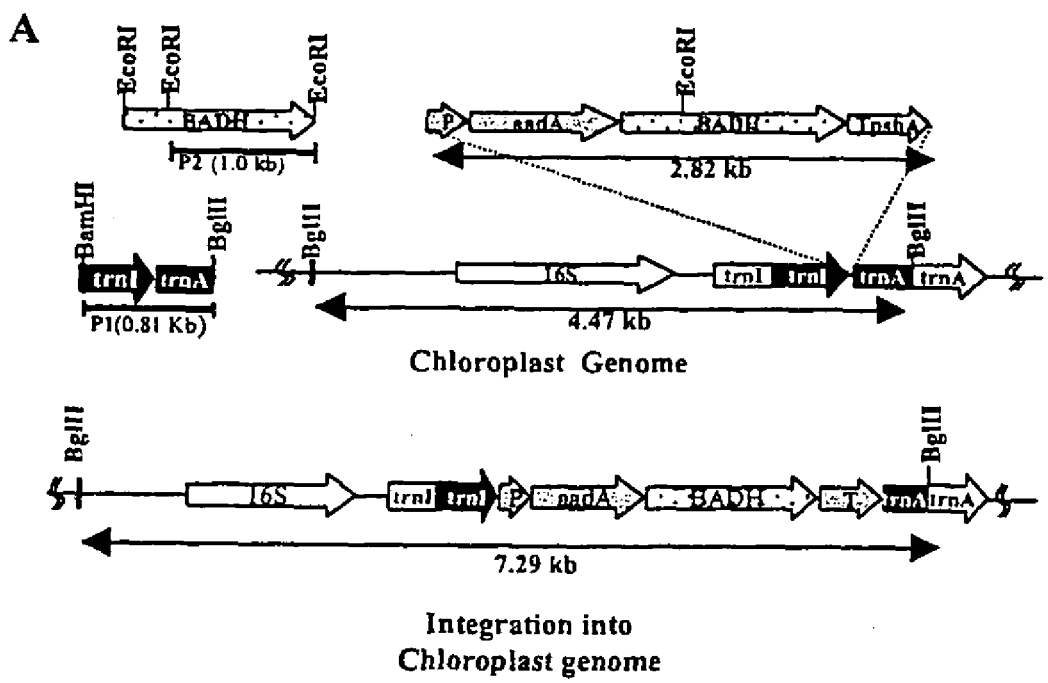
FIG. 5 shows the Southern analysis of transgenic plants. A: Probe P1 was used to confirm chloroplast integration of foreign genes. The 0.81 kb fragment was cut with BamHl and Bglll contains the flanking sequence used for homologous recombination. Untransformed control plants shuold generate 4.47 kb fragment and transformed plants should generate a 7.29 kb fragment. B: Lanes 1, untransformed Petit Havana; Lanes 7 pLD-BADH plasmid DNA or purified DNA or purified 1.0 kb Eco R1 BADH gene fragment. Lanes 2 through 6 of transgenic plants. Probe (P2) was used t confirm the integration of BADH gene.
Figure 5:
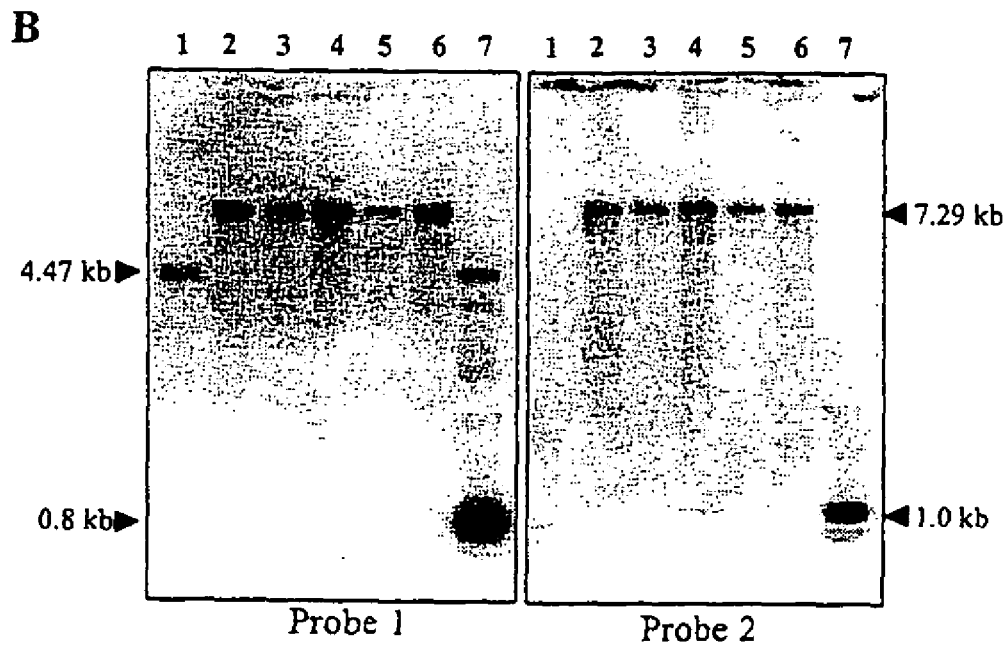

Southern blot analysis was performed using total DNA isolated from transgenic and wild type tobacco leaves. Total DNA was digested with a suitable restriction enzyme. Presence of a BglII cut site at the 3' end of the flanking 16S rRNA gene and the trnA intron allowed excision of predicted size fragments in the chloroplast transformants and untransformed plants. To confirm foreign gene integration and homoplasmy, individual blots were probed with the flanking chloroplast DNA sequence (probe 1, FIG. 5A). In the case of the BADH integrated plastid transformants, the border sequence hybridized with a 7.29 kbp fragment while it hybridized with a native 4.47 kbp fragment in the untransformed plants (FIG. 5B). The copy number of the integrated BADH gene was also determined by establishing homoplasmy in transgenic plants (Daniell et al. 1998; Guda et al. 2000). Tobacco chloroplasts contain about 10,000 copies of chloroplast genomes per cell. If only a fraction of the genomes was transformed, the copy number should be less than 10,000. By confirming that the BADH integrated genome is the only one present in transgenic plants, it could be established that the BADH gene copy number could be as many as 10,000 per cell.

DNA gel blots were also probed with the BADH gene coding sequence (P2) to confirm specific integration into the chloroplast genomes and eliminate transgenic plants that had foreign genes also integrated into the nuclear genome. In the case of the BADH integrated plants, the BADH coding sequence hybridized with a 7.29 kbp fragment which also hybridized with the border sequence in plastid transformant lines (FIG. 5B). This shows that the BADH gene was integrated only into the chloroplast genome and not the nuclear genome in transgenic lines examined in this blot. Also, this confirms that the tobacco transformants indeed integrated the intact gene expression cassette into the chloroplast genome and that no internal deletions or loop outs during integration occurred via homologous recombination.

Osmoprotection.

In higher plants accumulation of osmoprotectants during salinity and drought stress is a common phenomenon in their metabolic adaptation. Osmoprotectants help to protect plant organelles from osmotic shock as well as the cellular membranes from damage during stress (Nuccio et al. 1999). Among the osmoprotectants, glycine betaine is the most effective and is commonly present in a few families, including Chenopodiaceae and Poaceae. But most of the crop species including tobacco do not accumulate glycine betaine. Since synthesis and localization of glycine betaine is compartmentalized in chloroplasts, engineering the chloroplast genome for glycine betaine synthesis may provide an added advantage for chloroplast transgenic plants. BADH converts toxic betaine aldehyde to non-toxic glycine betaine which is the second step in the formation of glycine betaine from choline. By analyzing BADH enzyme activity, the expression of introduced BADH gene can be monitored. Since BADH is a NAD+ dependent, enzyme activity is analyzed for the formation NADH. The reaction rate is measured by an increase in absorbency at 340 nm resulting from the reduction of NAD+.

Figure 6:
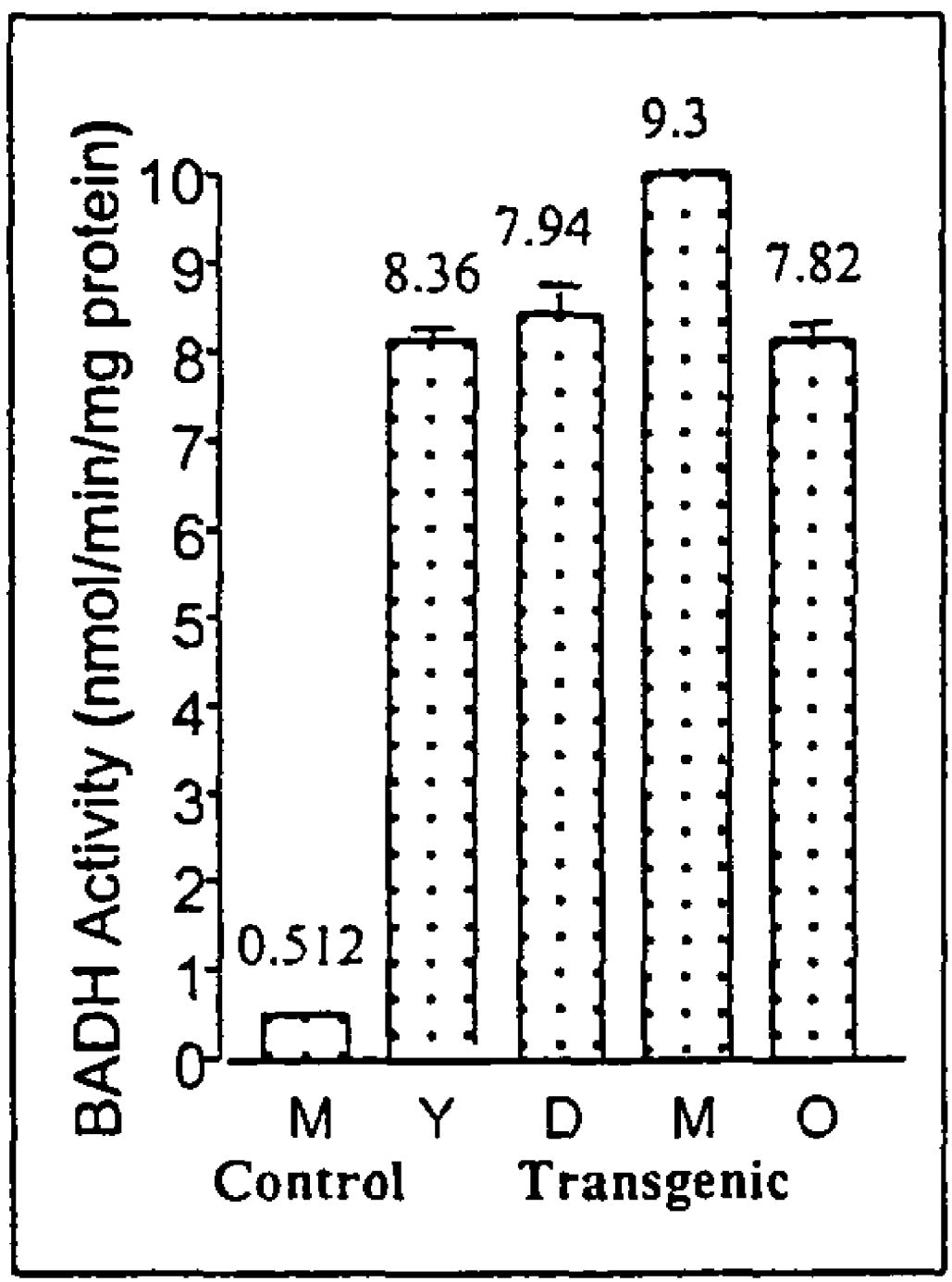
FIG. 6 shows BADH enzyme activity in different ages of leaves of transgenic tobacco plant. Proteins were extracted from 1-2 g leaves. Extracts were centrifuged at 10,000×G for 10 minutes and the resulting supernatant was desalted in small G-25 columns, and tested for assay (50 µg protein per assay). NAD+ dependent BADH enzyme was analyzed for the formation of NADH. Y, D, M and O represent young, developing, mature and old leaves, respectively.

BADH enzyme activity was assayed in crude leaf extracts of wild type and transgenic plants. Unlike previous reports, no purification with ammonium sulfate was necessary in order to perform the BADH assay. Crude extracts from chloroplast transgenic plants showed elevated activity (15-18 fold) compared to the untransformed tobacco (FIG. 6). The wild type tobacco showed low endogenous activity as reported previously (Rathinasababathy et al. 1994). BADH enzyme activity was investigated from young (top 3-4 leaves), mature (large well developed), developing leaves (in between young and mature) and bleached old leaves from transgenic plants. Crude leaf extracts from different developmental stages of the same transgenic plant showed differential activity with the most activity observed in mature leaves (18 fold over control) and least activity in older leaves (15 fold over control, as seen in FIG. 6). Unlike nuclear transgenic lines, crude extracts from different chloroplast transgenic lines did not show significant variation in BADH activity (data not shown).

Figure 7:
FIG. 7 shows the phenotypes of control (A) and chloroplast transgenic plants (B).
Figure 8:
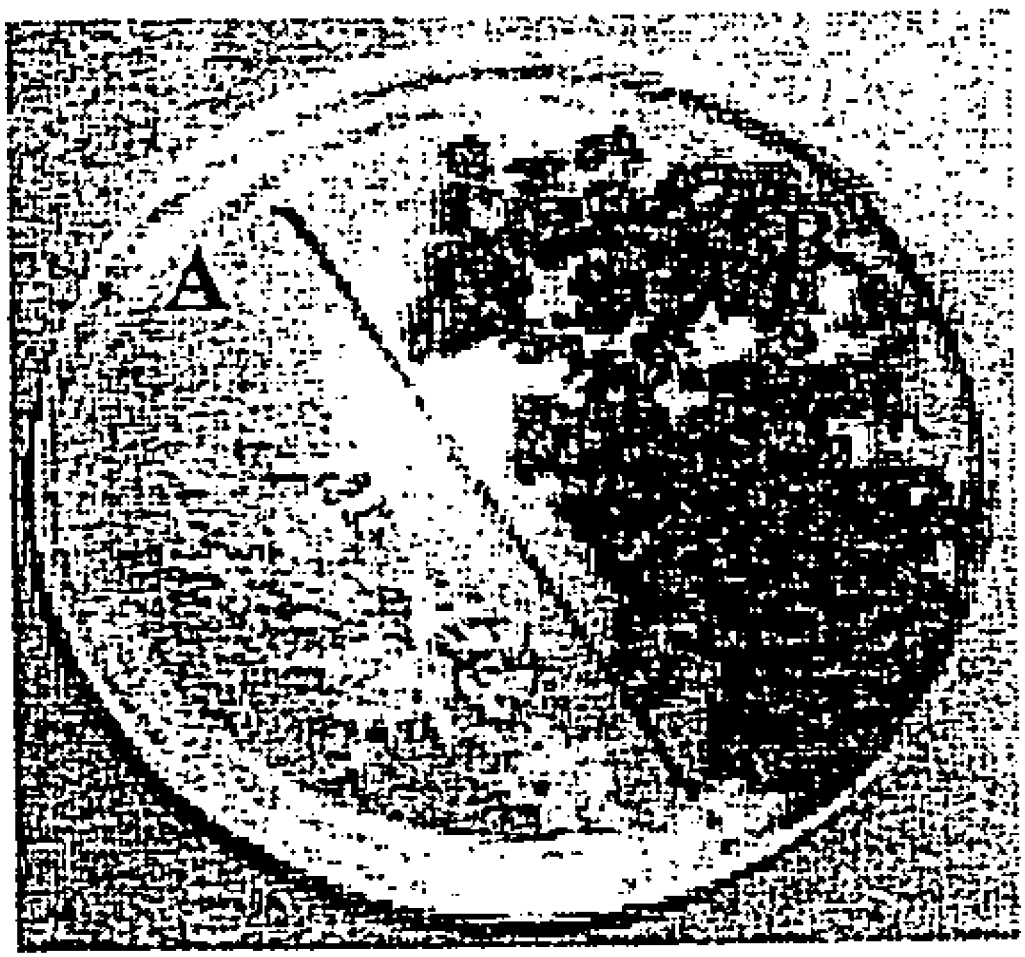
FIG. 8 shows the germination of control untransformed (a) and chloroplast transgenic (b) seeds on MS medium containing 500 µg/ml spectinomycin.
Figure 9A:
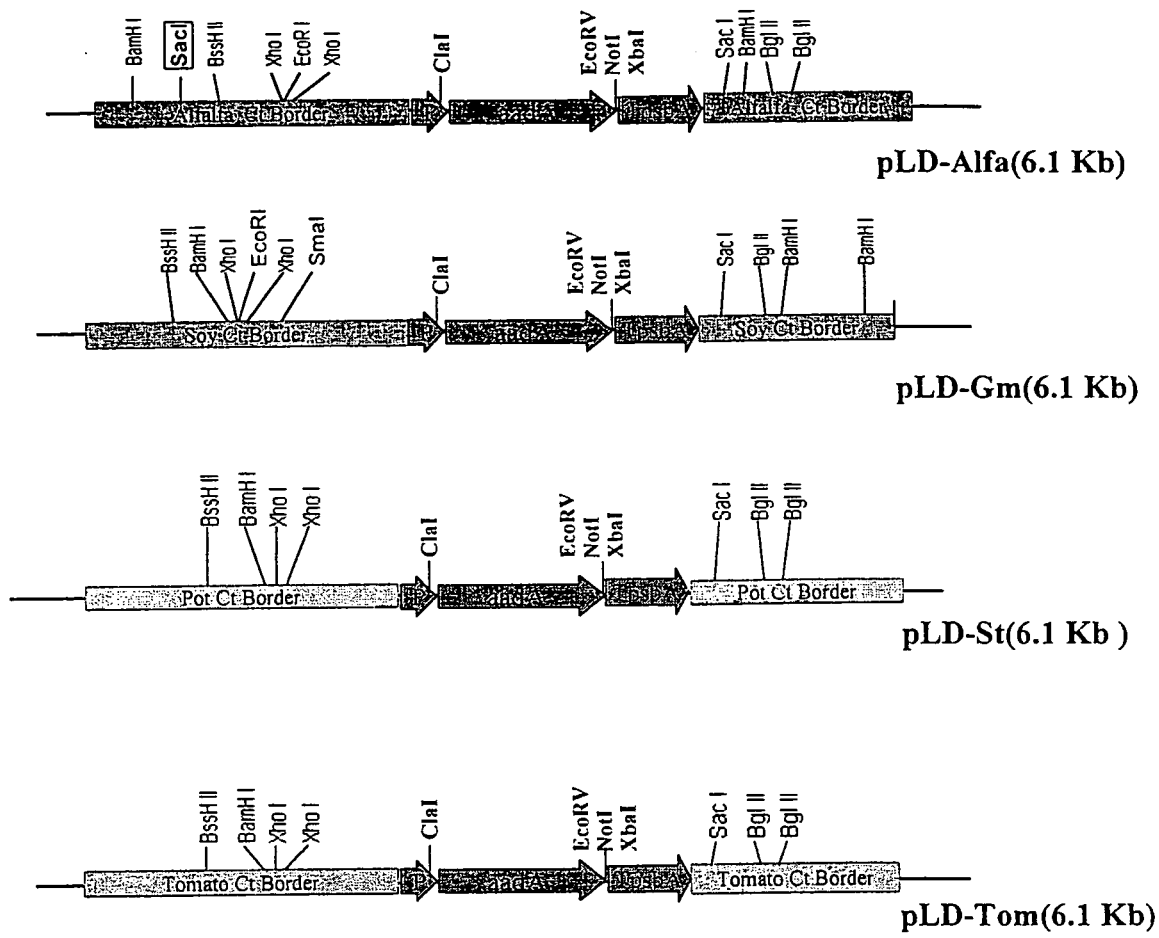
FIGS. 9A and B show the vectors for BADH selection in other plants.
Figure 9B:
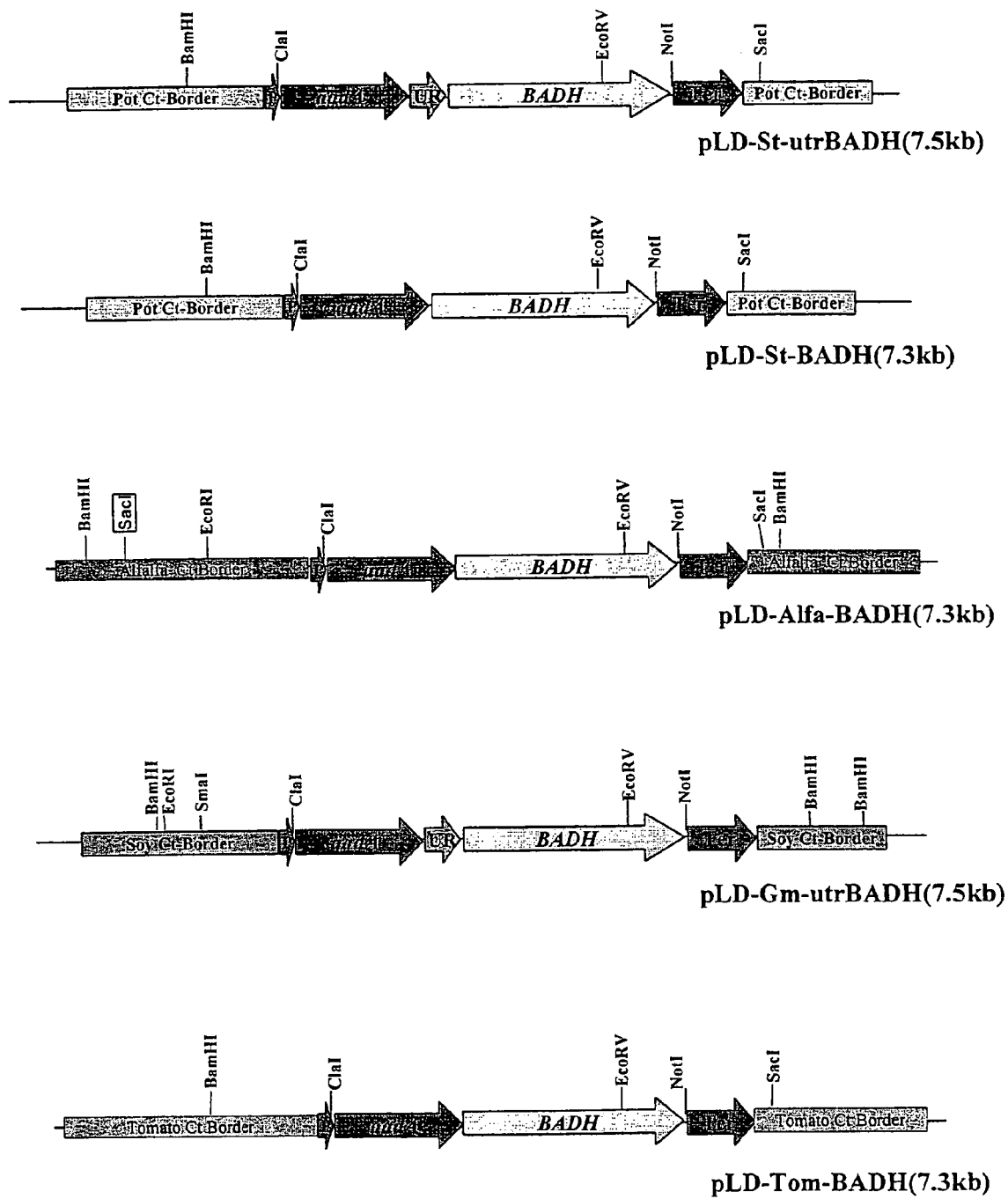

Lack of pleiotropic effects. Expression of BADH and resultant accumulation of glycine betaine did not result in any pleiotropic effects; transgenic plants are morphologically indistinguishable from control untransformed plants (FIG. 7). They grew normally, flowered and set seeds. Germination of seeds from untransformed plants in the presence of spectinomycin resulted in complete bleaching whereas seeds from the chloroplast transgenic plants germinated and grew normally (FIG. 8). Because untransformed seeds germinated in very high concentrations of betaine aldehyde (10-15 mM), no comparison between control and transgenic seeds could be made during germination on betaine aldehyde. This may be due to the presence of an active endogenous BADH or similar enzymatic activity in non-green plastids during germination. These results demonstrate that the introduced trait is stably inherited in the subsequent generation and that it is safe to use betaine aldehyde selection because of the lack of pleiotropic effects.

Application to Other Plants. This invention applies to any higher plants, such as monocotyledonous and dicotyledonous plant species. The plants that may be transformed via the universal vector with a antibiotic-free selectable marker maybe solanacious plants or plants that grow underground. Most importantly, this invention is applicable to the major economically important crops such as maize, rice, soybean, wheat, and cotton. A non-exclusive list of examples of higher plants which may be so transformed include cereals such as barley, corn, oat, rice, and wheat; melons such as cucumber, muskmelon, and watermelon; legumes such as bean, cowpea, pea, peanut; oil crops such as canola and soybean; solanaceous plants such as tobacco; tuber crops such as potato and sweet potato; and vegetables like tomato, pepper and radish; fruits such as pear, grape, peach, plum, banana, apple and strawberry; fiber crops like the *Gossypium* genus such as cotton, flax and hemp; and other plants such as beet, cotton, coffee, radish, commercial flowing plants, such as carnation and roses; grasses, such as sugar cane or turfgrass; evergreen trees such as fir, spruce, and pine, and deciduous trees, such as maple and oak.

The invention is exemplified in the following non-limiting examples.

EXAMPLE 1

A. Betaine Aldehyde Selection of Tobacco Chloroplast Transformation. Tobacco plant chloroplasts were transformed by the universal vector containing both a targeted gene of interest and the spinach betaine aldehyde dehydrogenase gene. The transformed cells were cultured in growth medium containing betaine aldehyde, a phytotoxic aldehyde. Since betaine aldehyde is lethal to all untransformed cells, such cells will not be regenerated in the growth medium. Therefore, all cells which grow in the growth medium containing betaine aldehyde are successfully transformed with the BADH gene lore importantly, such cells are successfully transformed with the targeted gene of interest.

B. Other possible plants. Other than tobacco, this invention can be practiced upon other monocotyledonous and dicotyledonous plants, including maize, rice, soybean, wheat, cotton, oat, barley, cucumber, muskmelon, watermelon, bean, cowpea, pea, peanut, canola, potato and sweet potato; tomato, pepper, radish, pear, grape, peach, plum, banana, apple, strawberry, flax, hemp, beet, coffee, radish, commercial flowing plants, such as carnation and roses; grasses, such as sugar cane or turfgrass; fir, spruce, and pine, maple and oak.

C. Other antibiotics that can be replaced. This example provides that the invention can replace all antibiotics as a selectable marker, including those listed in Molecular Biotechnology by Glick and Pasternak, page 437, Table 17.4.

D. Other targeted genes of interest. This invention provides that genes of interest expressing desirable traits are encoded by the targeted DNA sequence in the expression cassette.

EXAMPLE 2

Other antibiotic-free phytotoxic agents include phytotoxic aldehydes such as acetaldehyde, formaldehyde, proprionaldehyde, and butyraldehyde; herbicides such as triazines and cyanamide, including those listed in Molecular Biotechnology by Glick and Pasternak, page 459, Table 18.4. Also useful is light selection.

EXAMPLE 3

Other Genes of interest may be isolated from other organisms such as Sugar Beet and *E. Coli*.

EXAMPLE 4

Other Promoters can be used to drive expression of the genes, including the psbA promoter, the accD promoter, the 16SrRNA promoter, and those listed in U.S. Pat. No. 5,693,507 and International Publication No. WO99/10513, both to Daniell.

EXAMPLE 5

Other chloroplast vectors may be used in lieu of the universal vector, including those listed in U.S. Pat. Nos. 5,693,507 and 5,932,479 to Daniell.

EXAMPLE 6

Targeted Genes of Interest include: Polypepide pro-insulin, PBP synthetic polymer, Insulin, Human Serum Albumin, and Herbicide glyphosate. Other genes of interest include, but are not limited to the aminoglycosides listed in "Aminoglycosides: A Practical Review" by Gonzalez, L. S. and Spencer, J. P., American Family Physician, No. 8, 58:1811.

REFERENCES

Arntzen Ph.D., Charles J. (1997) *Public—Health Reports* 112: 190-197.

Bock R, Hagemann R. (2000) Extracellular inheritance: Plastid genomics: Manipulation of plastid genomes and biotechnology apparatus. Progress in Botany 6:76-90

Bogorad L (2000) Engineering chloroplasts: an alternative site for foreign genes, proteins, reactions and products. Trends in Biotechnology 18: 257-263.

Boynton J E, Gillham N W, Harris E H, Hosler J P, Johnson A M, Jones A R, Sanford J C (1988) Chloroplast transformation in *Chlamydornonas* with high velocity microprojectiles. Science 240: 1534-1538.

Brixey, P. J., Guda, H. and Daniell, H. (1997) *Biotechnol. Lett.* 19, 395-399.

Carlson, P. S. (1973) *Proc. Natl. Acad. Sci. USA* 70: 598-602.

Chaleff and Ray. (1984) *Science* 223:1148.

Comai, L., Faciotti, D., Hiatt, W., Thomson, G., Rose, R., and Stalker, D. (1983) *Science* 221:370.

Daniell H (1993) Foreign gene expression in chloroplasts of higher plants mediated by tungsten particle bombardment. Methods in Enzymology. 217: 536-556.

Daniell, H. (1997) Transformation and foreign gene expression in plants mediated by microprojectile bombardment. Meth. Mol. Biol. 62: 453-488.

Daniell H (1999A) GM crops: Public perception and scientific solutions. Trends in Plant Science 4: 467-469.

Daniell H (1999B) Environmentally friendly approaches to genetic engineering. In Vitro Cellular and Developmental Biology-Plant. 35: 361-368.

Daniell H (1999C) New tools for chloroplast genetic engineering. Nature Biotechnol. 17: 855-856.

Daniell H, Datta R, Varma S, Gray S, Lee S B (1998) Containment of herbicide resistance through genetic engineering of the chloroplast genome. Nature Biotechnol. 16: 345-348.

Daniell, H., Guda, C., McPherson, D. T., Xu, J., Zhang, X. and Urry, D. W. (1997) *Meth. Mol. Biol.*, 63:359-371.

Daniell, H., and Guda, C. (1997) *Chemistry and Industry,* pages 555-558.

Daniell, H., Krishnan, M. and McFadden, B. A. (1991) *Plant Cell Rep.* 9: 615-619.

Daniell, H., and McFadden. (1987) *Proc. Nat. Acad. Sci. (USA)* 84: 6349-6353.

Daniell, H., Vivekananda, J., Neilson, B., Ye, G. N., Tewari, K. K., and Sanford, J. C. (1990) *Proc. Nat. Acad. Sci. (USA)* 87: 88-92.

Daniell, H. Porobo Dessai, A., Prakash, C. S. and Moar, W. J. (1994) *NATO Asi Series*. Ed., J. H. Cherry. H86: 598-604.

Darkocsik, C., Donovan, W. P. and Jany, C. S. (1990) *Mol. Microbiol.* 4: 2087-2094.

Daniell, H., (1995) *Inform.* 6: 1365-1370.

Daniell, H., Ramanujan, P., Krishnan, M., Gnanam, A. and Rebeiz, C. A. (1983) *Biochem. Riophys. Res. Comun* 111: 740-749.

Daniell, H. and Rebeiz, C. A. (1982) *Biochem. Biophys. Res. Comun.* 106: 466-471.

Daniell, H. (1993) *Methods in Enzymology.* 217: 536-556.

Daniell, H. (1997a) *Meth. Mol. Biol.* 62: 453-488.

DeBlock, M., Botterman, J., Vandewiele, M., Docky, J., Thuen, C., Gossele, V., Movva, N. R., Thomson, C., Van Montagu, M., and Leemans, J. (1987) *EMBO J.* 6: 2513-2518.

De Cosa B, Moar W, Lee SB, Miller M, Daniell H (2000). Hyper-expression of *Bt* Cry2Aa2 operon in chloroplast leads to formation of insecticidal crystals. Nature Biotechnology, in press Eibl C, Zou Z, Beck A, Kim M, Mullet J, Koop U H (1999) in vivo analysis of plastid psbA, rbcL and rpl32 UTR elements by chloroplast transformation: tobacco plastid gene expression is controlled by modulation of transcript level and translation efficiency. The Plant Journal 19: 333-345.

Erickson et al. (1984) *Proc. Nat. Acad. Sci. (USA)* 81:3617.

Falco and Dumas. (1985) *Genetics* 109: 21.

Fischer N, Stampacchia O, Redding K, Rochaix J D (1996) Selectable marker recycling in the chloroplast. Mol. Gen. Genet. 251:373-380.

Fox J L (2000) GM food singled out for labeling in the U.S. Nature Biotechnol. 18: 375.

Gabard, J. M., Charest, P. J., Iyer, V. N. and Miki, B. L. (1989) *Plant Phys.* 91: 574-580.

Galloway and Mets. (1984) *Plant Physiol.* 74: 469.

Gloden and Haselkorn. (1985) *Science* 229: 1104.

Gonzalez and Spencer (1998) *American Family Physician.* 58:1811.

Guda, C., Zhang, X., McPherson, D. T., Xu, J., Cherry, J., Urry, D. W. and Daniell, H. (1995) *Biotechnol. Lett.* 17: 745-750.

Guda C, Lee S B, Daniell H (2000) Stable expression of biodegradable protein based polymer in tobacco chloroplasts. Plant Cell Rep. 19: 257-262.

Heifetz P (2000) Genetic engineering of chloroplast. Biochemie 82:655-666.

Hirschberg and McIntosh. (1993) *Science* 222: 1346.

Hodgson J (1999) Monarch *Bt*-corn paper questioned. Nature Biotechnol. 17: 627.

Hoyle B (1999) Canadian farmers seek compensation for genetic pollution. Nature Biotechnol. 17: 747-748.

Johanningmeier et al. (1987) *FEBS Lett* 211: 221.

Kanyand et al. (1994) *Plant Cell Reports* 14: 1-5.

Keeler K H, Turner C E, Bolick M R (1996) Movement of crop transgenes into wild plants. In Herbicide Resistant Crops, Duke (ed). CRC Press, pp. 303-330.

Keegstra K, Cline K (1999) Protein import and routing systems of chloroplasts. Plant Cell 11: 557-570.

Kin Ying et al. (1996) *The Plant Journal* 10: 737-743.

King, J. (1996) *Science* 274: 180-181.

Kota M, Daniell H, Varma S, Garczynski F, Gould F, Moar W J (1999) Overexpression of the *Bacillus thuringiensis* Cry2A protein in chloroplasts confers resistance to plants against susceptible and *Bt*-resistant insects. Proc. Natl. Acad. Sci. USA. 96: 1840-1845.

Laemmli, U. K. (1970) Nature 227: 680-685.

Langevin, S. A., Clay, K. and Grace, J. B. (1990) *Evolution* 44: 1000-1008.

Lewellyn and Fitt (1996) *Molecular Breeding* 2: 157-166.

Losey J E, Rayor L S, Carter M C (1999) Transgenic pollen harms monarch larvae. Nature. 399: 214.

Lu, Z., Kunnimalaiyaan, M. and Nielsen, B. L. (1996) *Plant Mol. Biol.* 32: 693-706.

Lyons, P. C., May, G. D., Mason, H. S., and Arntzen, C. J., (1996) *Pharmaceutical News* 3: 7-12.

Maier, R. M., Neckerman, K., Igloi, G. L. and Kössel, H. (1995) *J. Mol. Biol.* 251: 614-628.

May, G. D., Mason, H. S., Lyons, P. C. (1996) *American Chemical Society*, pp. 194-204.

Miele, L. (1997) *Elsevier Trends Journals*, Vol. 15.

Mikkelson, T. R., Anderson, B. and Jörgenson, R. B. (1996) Nature 380: 31.

Miki, B. I., Labbe, H., Hatori, J., Ouellet, T., Gabard, J., Sunchara, G., Charest, P. J. and Iyer, V. N. (1990) *Theoretical Applied Genetics* 80: 449-458.

McBride, K. E., Svab, Z., Schaaf, D. J., Hogan, P. S., Stalker, D. M. and Maliga, P. (1995) *Bio/Technology* 13: 362-365.

Nielsen, B. L., Lu, Z and Tewari, K. K. (1993) *Plasmid* 30: 197-211.

Nuccio M L, Rhodes D, McNeil S D, Hanson A D (1999) Metabolic engineering of plants for osmotic stress tolerance. Curr. Opinion in Plant Biology 2:128-134.

Oard, J. H., Linscombe, S. D., Braveramn, M. P., Jodari, F., Blouin, D. C., Leech, M., Kohli, A., Vain, P. Cooley, J. C. and Christou, P. (1996) *Mol. Breed.* 2: 359-368.

Peerenboorn E (2000) German health minister calls time out for *Bt* maize. Nature Biotechnol. 18: 374.

Penazloza, V., et al. (1995) *Plant Cell Reports* 14: 482-487.

Puchta H (2000) Removing selectable marker genes: taking the shortcut. Trends in Plant Science 5: 273-274.

Rathinasabapathy B, McCue K F, Gage D A, Hanson A D (1994) Metabolic engineering of glycine betaine sythesis: Plant betaine aldehyde dehydrogenases lacking typical transit peptides are targeted to tobacco chloroplasts where they confer aldehyde resistance. Planta. 193:155-162.

Rudraswamy, V., and Reichert, N. A. (1997) M.S. Thesis. Mississippi State Univ.

Rogers, S. O., and Bendich, A. J. (1988) in *Plant Molecular Biology Manual*, ed. Gelvin, S. B. and Schilperoot, R. A. (Kulwer Academic Publishers, Dordrecht, Netherlands) pp. A6:1-10.

Sambrook, J., Fritch, E. F. and Maniatis, T. (1989) in *Molecular cloning*. Cold Spring Harbor Press, Cold Spring Harbor, N.Y.

Sanford, J. C. (1988) *Trends In Biotech.* 6: 299-302.

Sankula, S., Braverman, M. P., Jordari, F., Linscombe, S. D. and Oard, J. A. (1996) *Weed Technol.* 11: 70-75.

Schultz, A., Wengenmayer, F. and Goodman, H. (1990) *Critical Review in Plant Sciences* 9: 1-15.

Shaner and Anderson, P. C., (1985), *Biotechnology in Plant Science*, 287.

Sidorov V A, Kasten D, Pang S Z, Hajdukiewicz P T J, Staub J M, Nehra, N S (1999) Stable chloroplast transformation in potato: use of green fluorescent protein as a plastid marker. Plant Journal 19: 209-216.

Sijmons, P. C., Cekker, B. M. M., Schrammeijer, B., Verwoerd, T. C., van den Elzen, P. J. M., Hoekema, A. (1990) *Biotechnology* 8: 217-221.

Stalker, et al. (1985) *J. Biol. Chem.* 260: 4724.

Stummann et al. (1988) *Physiologia Plantarum* 72:139-146.

Svab, Z. and Maliga, P. (1993) *Proc. Natl. Acad. Sci. (USA)* 90: 913-917.

Svab, Z., Hajdukiewicz, P. and Maglia, P. (1990) *Proc. Nat. Acad. Sci. (USA)* 87: 8526-8530.

Scott S E, Wilkinson M J (1999) Risks of transgene escape from transplastomic oilseed rape. Nature Biotechnology, 17: 390-392.

Svab Z, Hajdukiewicz P, Maliga P (1990) Stable transformation of plastids in higher plants. Proc. Natl. Acad. Sci. USA 87: 8526-8530.

Svab Z, Maliga P (1993) High frequency plastid transformation in tobacco by selection for a chimeric aadA gene. Proc. Natl. Acad. Sci. USA. 90: 913-917.

Umbeck, P. F., et al. (1991) *Econ. Entomology* 84: 1943-1950.

Urry, D. W., Nicol, A., Gowda, D. C., Hoban, L. D., McKee, A., Williams, T., Olsen, D. B. and Cox, B. A. (1993) in *Biotechnological Polymers: Medical. Pharmaceutical and Industrial Applications*, ed. Gebelein, C. G. (Technomic Publishing Co., Inc., Atlanta, Calif.), pp. 82-103.

Weretilnyk E A, Bednarek S, McCue K F, Rhodes D, Hanson A D (1989) Comparative biochemical and immunological studies of the glycine betaine synthesis pathway in diverse families of dicotyledons. Planta 178: 342-352.

Widner, W. R. and Whiteley, H. R (1989) *J. Bacteriol.* 171: 961-974.

Yadav, et al. (1986) *Proc. Natl. Acad. (USA)* 83: 4418-4422.

Ye, G. N., Daniell, H. and Sanford, J. C. (I-99o) *Plant Mol. Biol.* 15: 809-819.

Yeh, H., Ornstein-Goldstein, N., Indik, Z., Sheppard, P., Anderson, N., Rosenbloom, J., Cicilia, G., Yoon, K. and Rosenbloom, J. (1987) *Collagen Related Res.* 7: 235-247.

Zhang, X., Guda, C., Datta, R., Dute, R., Urry, D. W. and Daniell, H. (1996) *Plant Cell Reports* 15: 381-385.

Zhang, X., Guda, C., Datta, R., Dute, R., Urry, D. W., Danell, H. (1995) *Biotechnology Letters* 17: 1279-1284.

Zhang, X., Urry, D. W. and Daniell, H. (1996) *Plant Cell Rep.* 16:174-179.

*Current Protocols in Molecular Biology*, Asubel et al., eds., John Wiley and Sons, Inc. (1997) Vol. I, II and III.

*Herbicide Resistance Crops, Agricultural, Environmental, Economic, Regulatory and Technical Aspects*, Duke, S. O., eds., CRC Press, Inc. (1996).

*Herbicide Resistance in Plants, Biology and Biochemistry*, Powles, S. B., and Holtum, J. A. M., eds., CRC, Press, Inc. (1994).

*Molecular Biotechnology: Principles and Applications of Recombinant DNA*, Glick, B. R. and Pasternak, J. J., ASM Press, Washington, D.C., 1998.

*Peptides: Design, Synthesis, and Biological Activity*, Basava, C. and Anantharamaiah, G. M., eds., Birkhauser Boston, 1994.

*Protein Folding: Deciphering the Second Half of the Genetic Code*, Gierasch, L. M., and King, J., eds., American Association For the Advancement of Science (1990).

I claim:

1. A method of selecting for a transformed plant cell of a species that is naturally inhibited by betaine aldehyde, wherein said method does not require selection for successful transformants by detection of antibiotic resistance, said method comprising introducing into a plastid genome of a starting plant cell of said species an integration and expression cassette which comprises, as operably linked components, a 5' end of a plastid DNA spacer sequence, a 5' untranslated region (UTR) having a ribosome binding site, a DNA sequence encoding a plant betaine aldehyde dehydrogenase capable of detoxifying a betaine aldehyde in said transformed plant cell, a 3' regulatory region functional in said plastid, and a 3' end of a plastid DNA spacer sequence, wherein said method further comprises culturing said plant cell in a plant growth medium comprising said betaine aldehyde, and selecting said transformed plant cell comprising said plastid genome in which the DNA sequence encoding a detoxifying enzyme is expressed and hence is capable of growth in the presence of said betaine aldehyde.

2. The method of claim 1, further comprising introducing into said plastid genome at least one heterologous DNA sequence coding for a molecule of interest, said at least one heterologous DNA sequence being located between the 5' end and 3' end of the plastid DNA spacer sequence.

3. The method of claim 1, wherein said method further comprises regenerating a transformed plant from said transformed plant cell.

4. The method of claim 1, wherein said DNA sequence encoding a detoxifying enzyme is from sugar beet or spinach plants.

5. The method of claim 1, said 5' UTR comprising a promoter from a gene selected from the group consisting of 16S rRNA, psbA, accD and atpB.

6. The method of claim 1, wherein said plant betaine aldehyde dehydrogenase is a spinach betaine aldehyde dehydrogenase.

7. The method of claim 1, wherein said plant species is tobacco.

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: synthetic oligonucleotide GAGF

<400> SEQUENCE: 1
ccgcgttgtt tcatcaagcc ttacg                                    25

<210> SEQ ID NO 2
<211> LENGTH: 25
<212> TYPE: DNA
<213> ORGANISM: Artificial Sequence
<220> FEATURE:
<223> OTHER INFORMATION: synthetic oligonucleotide GAGR

<400> SEQUENCE: 2 aaaaccgtc ctcagttcgg attgc                                     25
```

8. A method of selecting for a transformed plant cell, said method comprising introducing into a plastid genome of a plant cell a transgene encoding a plant enzyme capable of detoxifying a non-antibiotic phytotoxic agent, wherein said method further comprises culturing said plant cell in a plant growth medium containing said non-antibiotic phytotoxic agent, and selecting said transformed plant cell that is capable of growth in the presence of said phytotoxic agent due to expression of said transgene inside a plastid, wherein said phytotoxic agent is a lethal aldehyde.

9. The method of claim 8, further comprising introducing into said plastid genome at least one heterologous polynucleotide, wherein said polynucleotide encodes a molecule of interest.

10. The method of claim 8, wherein said method further comprises regenerating a transformed plant from said transformed plant cell.

* * * * *